United States Patent
Nies

(10) Patent No.: US 9,849,211 B2
(45) Date of Patent: Dec. 26, 2017

(54) DIMENSIONALLY STABLE MOLDED BONE REPLACEMENT ELEMENT WITH RESIDUAL HYDRAULIC ACTIVITY

(71) Applicant: Innotere GmbH, Radebeul (DE)

(72) Inventor: Berthold Nies, Fränkisch-Crumbach (DE)

(73) Assignee: Innotere GmbH, Radebeul (DE)

( * ) Notice: Subject to any disclaimer, the term of this patent is extended or adjusted under 35 U.S.C. 154(b) by 0 days.

(21) Appl. No.: 15/021,354

(22) PCT Filed: Oct. 23, 2014

(86) PCT No.: PCT/EP2014/072784
§ 371 (c)(1),
(2) Date: Mar. 11, 2016

(87) PCT Pub. No.: WO2015/059240
PCT Pub. Date: Apr. 30, 2015

(65) Prior Publication Data
US 2016/0220726 A1    Aug. 4, 2016

(30) Foreign Application Priority Data
Oct. 23, 2013 (DE) .................. 10 2013 221 575

(51) Int. Cl.
| | | |
|---|---|---|
| *A61K 33/42* | (2006.01) | |
| *A61F 13/00* | (2006.01) | |
| *A61F 2/28* | (2006.01) | |
| *A61K 6/08* | (2006.01) | |
| *A61L 24/00* | (2006.01) | |
| *A61L 27/02* | (2006.01) | |
| *A61L 24/02* | (2006.01) | |
| *A61L 27/56* | (2006.01) | |
| *A61L 27/12* | (2006.01) | |
| *A61L 27/54* | (2006.01) | |
| *A61L 27/58* | (2006.01) | |

(52) U.S. Cl.
CPC ....... *A61L 24/0036* (2013.01); *A61L 24/0015* (2013.01); *A61L 24/0042* (2013.01); *A61L 24/02* (2013.01); *A61L 27/02* (2013.01); *A61L 27/12* (2013.01); *A61L 27/54* (2013.01); *A61L 27/56* (2013.01); *A61L 27/58* (2013.01); *A61L 2430/02* (2013.01)

(58) Field of Classification Search
None
See application file for complete search history.

(56) References Cited

U.S. PATENT DOCUMENTS

2012/0191214 A1* 7/2012 Nies .................. A61K 6/0023
623/23.62

FOREIGN PATENT DOCUMENTS

| WO | 2005084726 A1 | 9/2005 |
| WO | 2008148878 A2 | 12/2008 |
| WO | 2012101428 A1 | 9/2012 |

OTHER PUBLICATIONS

Heinemann et al.; Acta Biomaterilia 9 (2013); 6199-6207; available online Dec. 20, 2012.*
M. P. Hofmann et al.: "Carvable calcium phosphate bone substitute material", Journal of Biomedical Materials Research Part B: Applied Biomaterials, vol. 83B, No. 1, Jan. 1, 2007 (Jan. 1, 2007), pp. 1-8, XP055169146, ISSN: 1552-4973, DOI: 10.1002/jbm.b.30761.
Anja Lode et al.: "Fabrication of porous scaffolds by three-dimensional plotting of a pasty calcium phosphate bone cement under mild conditions", Journal of Tissue Engineering and Regenertative Medicine, vol. 8, No. 9, Aug. 30, 2012 (Aug. 30, 2012), pp. 682-693, XP055169132, ISSN: 1932-6254, DOI: 10.1002/term.1563.

* cited by examiner

*Primary Examiner* — Jeffrey T. Palenik
(74) *Attorney, Agent, or Firm* — Michael Soderman

(57) ABSTRACT

The invention relates to dimensionally stable molded bone replacement elements made of mineral bone cement with residual hydraulic activity that contain at least one share of hardened mineral bone cement and at least one share of unconverted or unhardened reactive mineral bone cement, wherein the share of hardened mineral bone cement is 5% to 90% by weight. The dimensionally stable molded bone replacement elements have at least 5% of the maximum value of the strength of a completely hardened bone cement comprised of the same mineral components and with the same structural characteristics and reach compressive strengths in the range of 2 to 200 MPa. They are substantially free of water and can be converted under biological conditions.

15 Claims, 4 Drawing Sheets

DIMENSIONALLY STABLE MOLDED BONE REPLACEMENT ELEMENT WITH RESIDUAL HYDRAULIC ACTIVITY

CROSS REFERENCE TO RELATED APPLICATIONS

This application is the U.S. national stage of International Application No. PCT/EP2014/072784, filed on Oct. 23, 2014, and claims the priority thereof. The international application claims the priority of German Application No. DE 10 2013 221 575.4 filed on Oct. 23, 2013; all applications are incorporated by reference herein in their entirety.

BACKGROUND

The invention relates to dimensionally stable molded bone replacement elements made of mineral bone cement with residual hydraulic activity, a method and a set for producing it, as well as its use as a technical, bioengineering and/or pharmaceutical product, especially as an alloplastic bone implant.

Only a temporary retention of the implant material in the body is frequently required when medical implants are used. Research has been done for several years on the development of bioresorbable implant materials so that an elaborate operation to remove utilized implant materials that cannot be broken down by the body can be dispensed with in implantation processes of that type. Bioresorbable materials have the characteristic that they are gradually broken down after being implanted in the body. The decomposition products that arise in the process are reabsorbed by the body to a great extent.

Implant materials can be broken down actively or passively. In the case of an active breakdown by the organism, the implant material is broken down via enzymatic or cellular mechanisms. This applies, as an example, to implant materials made of collagen or mineral bone cements based on calcium phosphates. An active breakdown of implant materials is especially desired when the breakdown takes place within the framework of natural metabolism and not on the basis of an inflammatory reaction.

Previous solutions for providing alloplastic molded bone replacement elements are mostly based on calcium phosphates that are manufactured via precipitation or through high-temperature processes (sintering of suitable starting materials at temperatures >500° C.). Production through high-temperature processes does in fact supply materials with a substantial similarity to bone minerals, but it leads to a heavy coarsening of the structure; the bioactivity and resorbability of a molded bone replacement element are negatively impacted because of that.

Mineral bone cements that harden in situ via a hydraulic setting reaction are a special form.

U.S. Pat. No. 6,642,285 B1 discloses a hydraulic cement for manufacturing bone implants that is comprised of three components that are matched to one another, which are supposed to harden into a macro-porous solid immediately after mixing to the extent possible. The first component is a calcium source that completely hardens within 60 minutes as a preference in combination with an aqueous solution and a hydrophobic liquid; the product no longer has any hydraulic activity after hardening.

WO 2008 148 878 A3 discloses pastes, suspensions or dispersions comprised of a resorbable mineral bone cement component and a carrier liquid that are substantially free of water. The pastes, suspensions or dispersions that are disclosed have a liquid to pasty consistency and are implanted in this form as bone cements or bone replacement materials; the setting reaction completely takes place after implantation as a preference.

Lode et al. (*J. Tissue Eng. Regen. Med.* 2012) disclose that water-free, pasty preparations made of mineral bone cements can be printed via a printing process into porous molded elements that can subsequently be hardened into solid molded elements by putting them in aqueous solutions (to the extent described in the literature).

Surprisingly, it was found that molded elements that are manufactured in that way have especially good mechanical characteristics when the hardening does not take place in aqueous solutions, but instead in a saturated steam atmosphere at ambient temperatures or slightly increased temperatures (25-75° C.), especially below the sintering temperature.

The known solution suggestions have the situation in common that none of them involve residual hydraulic activity. Residual hydraulic activity is above all desirable based on biological conditions, because then part of the setting reaction of the cement-type mineral preparation takes place under biological conditions after implantation. Greater bioactivity can be achieved in this way.

Moreover, a stimulating effect on the osteogenic cells, which can be supported by an individualized adaptation to the bone defect of the patient, is desirable.

The instant invention is therefore based on the object of providing dimensionally stable molded bone replacement elements manufactured without using a ceramic-sintering step that are shaped under controlled conditions and that are solidified via a hydraulic setting process to the degree that adequate dimensional stability is ensured for storage, transport and the respective implantation conditions; the molded bone replacement elements are only completely hardened during and/or after the implantation, though.

SUMMARY

The invention relates to dimensionally stable molded bone replacement elements made of mineral bone cement with residual hydraulic activity that contain at least one share of hardened mineral bone cement and at least one share of unconverted or unhardened reactive mineral bone cement, wherein the share of hardened mineral bone cement is 5% to 90% by weight. The dimensionally stable molded bone replacement elements have at least 5% of the maximum value of the strength of a completely hardened bone cement comprised of the same mineral components and with the same structural characteristics and reach compressive strengths in the range of 2 to 200 MPa. They are substantially free of water and can be converted under biological conditions.

DETAILED DESCRIPTION

The problem is solved as per the invention by dimensionally stable molded bone replacement elements made of mineral bone cement with residual hydraulic activity that are comprised of
  a) at least one share of hardened mineral bone cement,
  b) at least one share of unconverted or unhardened reactive mineral bone cement,
wherein the dimensionally stable molded bone replacement element has at least 5% of the maximum strength value of a completely hardened mineral bone cement made of the same components and with the same structural characteristics, in particular the same porosity, wherein the dimensionally stable molded bone replacement elements that can be converted under biological conditions—37° C. and water saturation—contain a share of hardened mineral bone cement of 5 to 90 percent by weight, from 10 to 80 percent by weight as a special preference, and from 30 to 70 percent by weight as a very special preference, wherein the dimensionally stable molded bone replacement elements have a compressive strength in the range of 2 to 200 MPa and wherein the dimensionally stable molded bone replacement elements are substantially free of water.

Mineral bone cements are made up of at least one reactive mineral or organo-mineral solid component (bone cement component) that can harden into a solid with low solubility when coming into contact with an aqueous solution or after being put into an aqueous solution in a hydraulic setting process. Reactive mineral bone cements exclusively mean here that the at least one reactive mineral bone cement component has not yet been chemically converted with water to form a hardened mineral bone cement. The reactive mineral bone cement components are advantageously used in the form of powder mixtures that are intensively mixed; the formation of a dimensionally stable molded bone replacement element with a homogeneous composition is encouraged by that.

Residual hydraulic activity means, in the sense of the invention, the qualitative capability of a synthetic molded bone replacement element as per the invention to enter with the addition of water and/or a component containing water into a chemical reaction, i.e. a setting process, that can be interrupted by withholding water before the complete conversion of the reactive components has been achieved; a hydration of the residual reactive mineral bone cement component takes place once again via renewed contact of a synthetic molded bone replacement element as per the invention with water, which causes the interrupted setting process to be continued. The renewed contact with water and/or a component containing water of a synthetic molded bone replacement element as per the invention with residual hydraulic activity only takes place immediately before its use or during or after its use, and thus during or after implantation in the body.

As a preference, the dimensionally stable molded bone replacement element has at least 5% of the maximum value of the strength of a completely hardened, dimensionally stable molded bone replacement element made up of the same mineral bone cement components and with the same structural characteristics, especially the same porosity. They have enough dimensional stability at that point in time to be able to withstand the mechanical loads involved in storage and transport, for instance. As a preference, the dimensionally stable molded bone replacement elements have 15%, 25% as a special preference, 50% of the maximum value of the strength as a very special preference, and even more preferred >75% of the maximum value of the strength of a completely hardened, dimensionally stable molded bone replacement element made of the same mineral bone cement components and with the same structural characteristics, especially the same porosity.

The dimensionally stable molded bone replacement elements, which can be converted under biological conditions—37° C. and water saturation—preferably contain a share of hardened mineral bone cement of 5 to 90 percent by weight, 10 to 80 percent by weight as a special preference and 30 to 70 percent by weight as a very special preference.

The dimensionally stable molded bone replacement elements with residual hydraulic activity have compressive strengths of 2 to 200 MPa, from 5 to 200 MPa as a special preference, and from 10 to 200 MPa as a very special preference, and they are therefore comparable to a molded bone replacement element without residual hydraulic activity.

The dimensionally stable molded bone replacement elements with residual hydraulic activity have compressive strengths in a range of 2 to 100 MPa, in a range of 3 to 50 MPa as a special preference, in a range of 5 to 25 MPa as a very special preference, and they are therefore comparable to a molded bone replacement element without residual hydraulic activity.

Surprisingly, it turned out that dimensionally stable molded bone replacement elements that contain a share of approx. 80% of a reactive mineral bone cement component that has not yet been chemically converted (with reference to the starting content) already achieves 75% of the maximum compressive strength of a molded bone replacement element with a complete chemical conversion of the mineral bone cement component. As a particular surprise, it turned out that the dimensionally stable molded bone replacement elements that contain a share of approx. 50% of a reactive mineral bone cement component that has not yet been chemically converted already achieves the maximum compressive strength of a molded bone replacement element with a complete chemical conversion of the mineral component.

A universal testing machine such as that of the company Hegewald & Peschke, utilizing a load cell of 20 kN, for instance, with a feed rate of 1 mm/min, for example, can be used to determine the compressive strength of the molded bone replacement element as per the invention. The material conversion can be determined via x-ray diffractometry (XRD) in dependence upon the hardening duration at a certain temperature and humidity. The Rietveld method can be used for quantification. The Rietveld method serves to provide a quantitative phase analysis, and thus the quantitative determination of the crystalline components of a powdery sample.

The dimensionally stable molded bone replacement elements are substantially free of water as per the invention.

As a preference, the at least one share of reactive mineral bone cement that has not been converted or hardened contains a reactive mineral bone cement component that has not been converted or hardened with a share of at least 10 percent by weight, at least 20 percent by weight as a special preference, at least 30 percent by weight as a very special preference, and at least 50 percent by weight as even more of a preference.

It is advantageous that the dimensionally stable molded bone replacement element has a high level of biological activity. Biological activity designates, as per the invention, the characteristic of the dimensionally stable molded bone replacement element to advantageously form a crystal structure that is more similar to the bone during hardening under biological conditions. A bone-like nanocrystalline structure of the mineral structures that are formed in the setting process is an essential prerequisite for their interaction with the organic and cellular elements of the new bone being formed. That is why hardening of the dimensionally stable molded bone replacement element that goes as far as possible after implantation in the body under biological conditions is strived for. The greater the share of a reactive mineral bone cement component that has not been converted or hardened, the greater the biological activity. A dimensionally stable molded bone replacement element with the appropriate strength and biological activity can be provided in that way that is coordinated to the requirements of the respective clinical application area.

The dimensionally stable molded bone replacement elements preferably have an overall porosity of between 20% and 90%.

The overall porosity is the sum of the macro-porosity (macroscopically visible pores, >approx. 100 μm) and the micro and nano-porosity (only microscopically visible pores, <approx. 10 μm or <approx. 1 μm) of the dimensionally stable molded bone replacement elements. The macropores, as contained in printed, dimensionally stable 3D molded bone replacement elements, as an example, are particularly significant for growth of cells and tissue structures into the molded element. The micro and nano-pores are a result of bringing together the reactive mineral bone cement that has not been converted or hardened and its processing conditions. They are crucial for the specific surface of the dimensionally stable molded bone replacement elements and therefore for the absorption capability for biological molecules and the interaction with bone cells.

In one embodiment, the dimensionally stable molded bone replacement elements exist in the form of granules; the individual granules have a size of >100 μm and <10 mm.

The granules with biological activity can be advantageously used to fill out bone defects. The granules form a crystal structure that is more similar to the bone after implantation in the body with a setting reaction that takes place under biological conditions to a very great extent.

Larger molded bone replacement elements, adapted to the corresponding defect location, can be advantageously prepared from the granules via shaping processes (e.g. pressing them in a mold). In addition, the ease of manufacturing the granules, their high level of bioactivity and their relatively high compressive strength are advantageous.

The dimensionally stable molded bone replacement element will preferably have the shape of a printed 3D molded element. Printed 3D molded elements will preferably obtain their structure via a 3D printing process; both the external shape and the pore structure can be specified in very broad areas because of that. As a preference, they will have a geometric external shape, especially in the form of a cylinder or rectangular block. Other preferred shapes are wedges, disks, cones anatomically adapted to the bones or shapes that are known from the implantation of cages for the spinal column, for instance. A 3D molded bone replacement element as per the invention is preferably made up of several successive layers (stacked) that can accommodate various shapes, for instance circular, oval and angular shapes. The individual layers are comprised of sections that are arranged in such a way that spaces arise between the sections; a contiguous (interconnecting) macro-porosity arises because of that, wherein the macro-porosity is in a range of 20% to 90%.

Specific pore arrangements and specific pore volumes can be advantageously produced via 3D printing processes. This advantageously makes the design of directional pores possible, in particular, so the path for the new bones growing in to bridge over a bone defect can be reduced to a minimum.

The problem is solved as per the invention via a method for manufacturing dimensionally stable molded bone replacement elements with residual hydraulic activity comprised of the following steps:
a) Mixing a reactive mineral bone cement to create a moldable bone cement substance,
b) Shaping the bone cement substance to form a molded bone replacement element,
c) Putting the molded bone replacement element into contact with an aqueous solution or a water (steam) saturated environment so that a setting process is initiated and the molded bone replacement element achieves at least 5% of the maximum value of the strength of a completely hardened bone replacement material made of the same components and with the same structural features, especially the same porosity,
d) Terminating the setting process by substantially withdrawing water so that the dimensionally stable molded bone replacement element will contain a share of hardened mineral bone cement of 5 to 90 percent by weight, from 10 to 80 percent by weight as a special preference, and from 30 to 70 percent by weight as a very special preference, and that the dimensionally stable molded bone replacement element is substantially free of water.
e) If necessary, drying the molded bone replacement element, i.e. removing auxiliary materials, residual water and/or water-soluble solvents contained in it that were used to substantially withdraw the water.

The problem is solved via a method for manufacturing dimensionally stable molded bone replacement elements with residual hydraulic activity comprised of the following steps:
a) Mixing a reactive mineral bone cement to create a moldable bone cement substance,
b) Shaping the bone cement substance to form a molded bone replacement element,
c) Putting the molded bone replacement element into contact with an aqueous solution or a water (steam) saturated environment so that a setting process is initiated and the molded bone replacement element achieves at least 5% of the maximum value of the strength of a completely hardened bone replacement material made of the same components and with the same structural features, especially the same porosity,
d) Terminating the setting process by substantially withdrawing water so that the dimensionally stable molded bone replacement element will contain a share of hardened mineral bone cement of 5 to 90 percent by weight, from 10 to 80 percent by weight as a special preference, and from 30 to 70 percent by weight as a very special preference, and that the dimensionally stable molded bone replacement element is substantially free of water.

As a special preference, the molded bone replacement element is dried via the removal of auxiliary materials, residual water and/or water-soluble solvents contained in it that were used to substantially withdraw the water.

Surprisingly, it turned out that the hydraulic setting process and the hardening of a synthetic molded bone replacement element associated with that can be interrupted by the substantial withdrawal of water (i.e. the complete removal of the share of physically bound and condensed water) from a molded bone replacement element as per the invention. A molded bone replacement element as per the invention exists in the form of a dimensionally stable structure that has residual hydraulic activity because of the interruption of the setting process.

A major advantage is that the molded bone replacement elements as per the invention can be subjected to plastic deformation before the first time they are brought into contact with water or a water (steam) atmosphere, but a dimensionally stable molded bone replacement element with residual hydraulic activity arises after the first time they are brought into contact with water or a water (steam) atmosphere and the premature interruption of the setting reaction whose hardness and brittleness can still be significantly below that of a completely hardened molded bone replacement element of the same mineral composition and with the same structural features, especially the same porosity. The molded bone replacement element as per the invention has sufficient mechanical strength for transport, storage and implantation. The shaping and/or structuring of a synthetic molded bone replacement element as per the invention into structured preforms with residual hydraulic activity advantageously makes it easier for the final user (e.g. surgeon) to adapt an implant based on a synthetic molded bone replacement element as per the invention to the defect of the bone in a positive-locking way, because it turned out that incompletely hardened molded elements as per the invention (with residual hydraulic activity) can be reworked especially well during an operation, for instance via carving with surgical instruments (e.g. scalpel), which, as experience has shown, is very difficult or impossible under OP conditions with commercially available molded ceramic elements.

The reactive mineral bone cements are obtained via intensive mixing of at least one powdery, reactive mineral bone cement component with a carrier liquid so that a homogeneous, moldable bone cement substance is obtained in the form of a pasty dispersion.

The pasty dispersions for manufacturing the dimensionally stable molded bone replacement element can be subjected to various methods of shaping; the composition of dispersions and their physical characteristics are matched to the shaping method. As an example, dispersions with a lower viscosity are used for casting methods than is the case for 3D printing methods. Preferred methods are oriented towards the desired shape and function of the molded bone replacement elements that are strived for.

As a preference, a paste capable of plastic deformation and containing at least one reactive mineral bone cement component that is dispersed in a carrier liquid is shaped by the effects of tensile and/or compressive forces in the form of rolling, printing (e.g. flatbed printing, porous printing, relief printing, intaglio printing, in accordance with DIN 16500, screen printing, offset printing, ink-jet printing, among others), extrusion, casting, coating with a doctor knife, granulation and other shaping methods that are known to a person skilled in the art.

Cylinders, blocks or wedges are preferred shapes of the molded bone replacement elements. They can be obtained, as an example, via casting or pressing in a corresponding negative mold. They can be hardened in the mold (see below), removed from the mold after reaching adequate post-removal strength and, if necessary, processed further until the desired degree of hardening is obtained.

Porous molded elements with different external geometries and randomly distributed macro-porosity are a further preferred type of molded bone replacement elements. Molded elements of that type can be obtained in a different way by putting a pasty bone cement dispersion containing a filler (e.g. sugar, salt, ammonium carbonate, polymer particles) that are readily soluble in water into a specified mold. The filler can be removed during or after the hardening via extraction or evaporation, and it can leave a porous structure behind in the process. The shaping can also take place after the hardening by first producing a larger molded element and creating the desired molded element in the implant size via subsequent processing (e.g. milling, sawing etc.).

Porous molded elements with a defined and especially interconnected porosity are an especially preferred form of molded bone replacement elements. Molded bone replacement elements of that type are of special clinical interest, because the goal of the bone integration that is to be complete and as quick as possible can only be achieved with an interconnecting porosity, and this bone integration can only take place in an especially quick manner when the path for the bone in-growth is as short as possible, and thus when the pores are in a straight line to the extent possible and run in a targeted way through the molded element. This goal can be achieved with the material and method as per the invention, especially via the 3D printing.

The paste that can be subjected to plastic deformation or, more specifically, the molded element created from that in the shaping step is brought into intimate contact in a subsequent step, preferably in a gradual way, with an aqueous solution or pure water or, as a special preference, a water (steam) atmosphere, to initiate the setting process. Surprisingly, it turned out that dispersions made of bone cement powder in a water-free carrier liquid with a high level of solid content can be processed to become large molded elements in one shaping step via 3D printing, as an example, without changing their geometric shape during the production and further processing. It is possible to first manufacture any number of molded elements and to jointly subject them in a subsequent step to the initiation of the setting process.

As a preference, the dimensionally stable molded bone replacement element is put into contact with an aqueous solution or a water (steam) saturated environment so that it achieves at least 5%, preferably 15%, very preferably 25%, especially preferably 50%, even more preferably >75% of the maximum value of the strength of a completely hardened bone replacement material made of the same components and with the same structural features, especially the same porosity.

The dimensionally stable molded bone replacement element is preferably put into contact with an aqueous solution or a water (steam) saturated environment for a period of time of 0 to 672 h.

The aqueous solution contains, as a preference, at least one additive selected from a buffer solution, an organic and/or an inorganic salt, a cell preparation (preferably stem cells, osteoprogenitor cells), an active biological, recombinant or pharmacological substance, nucleic acid (RNA or DNA), mixtures of nucleic acids, an amino acid, a modified amino acid, a vitamin and mixtures of them.

The aqueous solution advantageously contains a buffer solution; a pH value is set in a fixed way in the aqueous solution because of that. Various buffer solutions are known to a person skilled in the art. He will select a suitable buffer solution comprised of physiologically compatible components in dependence upon the pH value to be set. In addition, the aqueous solution can contain other inorganic and/or organic salts that do not have a buffer effect themselves. As a preference, the buffer solution and the other salts are selected from phosphates, citrates, acetates, chlorides, sulfates and borates. Preferred cations are alkali and alkaline earth metal ions, ammonium ions and guanidine.

As a special preference, the aqueous solution contains a solution of amino acids and/or modified amino acids, especially phosphorylated amino acids, and phosphoserine as a very special preference.

The hardening advantageously takes place in that way under defined (similar to those of the human body) biological conditions and nevertheless outside of the body by incubating the molded bone replacement element in a (defined biological) solution before implantation.

The active pharmacological substances are advantageously absorbed by the molded elements and/or adsorbed in dependence upon the type of active substance. The adsorption is dependent upon the specific surface of the molded elements. A more effective and more practical method is provided by the addition of active substances in the hardening phase instead of to molded elements that have set with finality. Some preferred active (biological and pharmacological) substances advantageously influence the nanostructure and therefore the specific surface of the molded elements. They are, on the one hand, specifically bound and lead, on the other hand, to a finer nanostructure, which, among other things, improves the mechanical characteristics, increases the resorbability and, in the case of active substances, additionally controls the delivery.

Water that can be substantially withdrawn is understood to mean, as per the invention, physically bound or condensed water. As a preference, the water is substantially withdrawn via the variation of physical environmental parameters (e.g. a reduction in pressure and/or increase in temperature or freeze drying) and/or via contact with a water-soluble solvent, preferably short-chain alcohols such as methanol, ethanol, isopropanol and/or propanol. Ketones, e.g. acetone, lactones such as γ-butyrolactone, lactames such as N-methyl-2-pyrrolidone, nitriles such as acetonitrile, nitro compounds such as nitromethane, tertiary carboxylic acid amides such as dimethylformamide, urea derivatives such as tetramethylurea or dimethyl propylene urea (DMPU), sulfoxides such as dimethylsulfoxide (DMSO), sulfones such as sulfolane, and carbonates such as dimethyl carbonate or ethylene carbonate can likewise be used to withdraw water.

In contrast to the substantial withdrawal of water via the variation of physical environmental parameters (e.g. reduction in pressure and/or increase in temperature or freeze drying) or via contact of the synthetic bone replacement material with a water-soluble solvent (e.g. solvent replacement of water with acetone), the water can also be substantially withdrawn via its consumption in the chemical setting reaction. In that case, the complete conversion of the existing share of physically bound water into chemically bound water suffices; less water is available in a defined way than would be necessary for a complete conversion in a complete setting reaction.

As a preference, not only water will be substantially withdrawn via the contact of the dimensionally stable molded bone replacement element with a water-soluble solvent; the carrier liquid and other auxiliary materials will also be washed out depending on the type of water-soluble solvent that is used. A person skilled in the art will preferably select the water-soluble solvent in accordance with the solubility characteristics of the carrier liquid and auxiliary materials that are used. The carrier liquid and the auxiliary materials will preferably be completely washed out of the dimensionally stable molded bone replacement element. A partial residue of the carrier liquid and/or the auxiliary materials in the dimensionally stable molded bone replacement element as per the invention is not ruled out because of that. Through the use of biocompatible materials as the carrier liquid and auxiliary materials, the use of dimensionally stable molded bone replacement elements of that type is also made possible in the human body.

The water is substantially withdrawn as a preference when the dimensionally stable molded bone replacement element contains a share of hardened mineral bone cement of 5 to 90 percent by weight, 10 to 80 percent by weight as a special preference and 30 to 70 percent by weight as a very special preference.

The dimensionally stable molded bone replacement element is put into contact or washed with a water-soluble solvent until the dimensionally stable molded bone replacement element is substantially free of water. According to a special design form of the invention, the dimensionally stable molded bone replacement element is put into contact or washed with different solvents (mixed).

The molded element with residual hydraulic activity that is obtained can be dried after the substantial withdrawal of water via the variation of physical environmental parameters (e.g. an increase in temperature and/or a reduction in pressure, freeze drying) to remove auxiliary materials, residual water and water-soluble solvents contained in it that were used to substantially withdraw water.

As a basic principle, the water removal, washing and drying can also take place under different conditions and with other solvents. The selection of a suitable solvent for the water removal and washing of the molded element will be obvious to a person skilled in the art in dependence upon the selected carrier liquids and auxiliary materials and in an appropriate way for the planned usage. Suitable washing and drying conditions likewise result from technical considerations regarding the auxiliary materials that are chosen (including safety-related and industrial-safety-related considerations), and a person skilled in the art will be familiar with them.

In a special design form of the invention, the setting reaction of the molded elements is carried out in several steps and/or with various aqueous solutions and/or a steam atmosphere. The mineral bone cement is first subjected to a shaping process for this; the shape of the bone implant is roughly specified or the final shape (net shape) is already established. After that, the setting process of the molded element for a dimensionally stable molded bone replacement element takes place via contact with an aqueous solution and/or a steam atmosphere. The setting process is interrupted at a specified point in time (or after reaching a defined degree of conversion)—before the complete conversion— by the withdrawal of water as per the invention. At a later point in time, the setting process is continued via renewed contact with an environment containing water or steam. This procedure makes it possible to carry out the setting process in successive steps while changing the reaction conditions, especially in different aqueous solutions. The setting reaction can consequently be carried out in an advantageous way under different and/or defined conditions. The dimensional stability of the molded element can be achieved in a first step for that. The interruption and resumption of the setting process can take place as frequently as desired. The dimensionally stable molded bone replacement element can finally be completely hardened in a last setting reaction. In particular, the manufacturer of the molded element can create a low-grade hardened molded bone replacement element in a first step. Starting from this pre-product, a processor taking it further can carry out a partial or complete hardening, for instance in the presence of defined active biological (cells, tissues), recombinant and/or pharmacological substances and therefore create the final product.

In accordance with the invention, the dimensionally stable molded bone replacement element is both a low-grade hardened molded bone replacement element and a partially or completely hardened molded bone replacement element, in so far as it was converted into a dimensionally stable state or molded element in an intermediate step via water withdrawal before the a complete setting reaction.

Low-grade hardening means, in the sense of the invention, a dimensionally stable molded element whose setting reaction was interrupted at an earlier point in time, especially at a point in time at which less than 30% of the hydraulically active components were converted. The point in time is preferably chosen in such a way that the molded element can be further processed without damage.

As a preference, a substance from the group of silicates, phosphates, sulfates, carbonates, oxides and/or hydroxides in combination with calcium ions, magnesium ions and/or strontium ions, which can set in a hydraulic setting process to form a solid of low solubility when put into contact with an aqueous solution or after addition to an aqueous solution, is used as at least one reactive mineral bone cement component for mixing the reactive mineral bone cement. Bone cement components that set to form calcium phosphates and/or magnesium phosphates are especially preferred.

As a preference, the reactive mineral bone cement component contains calcium and/or magnesium sales of orthophosphoric acid.

Reactive mineral bone cement components containing mixtures of calcium phosphates and/or magnesium phosphates with carbonates, oxides or hydroxides of calcium, magnesium or strontium are likewise especially preferred.

Reactive mineral bone cement components containing mixtures of carbonates, oxides or hydroxides of calcium, magnesium or strontium with alkali phosphates (mono, di and tri-alkali phosphates), mono and di-ammonium phosphates or alkali silicates.

As a preference, the reactive mineral bone cement is mixed with a carrier liquid to form a moldable bone cement substance. As a preference, the carrier liquid is an organic, water-free substance into which the at least one reactive mineral bone cement component has been dispersed.

As a preference, the organic carrier liquid is selected in such a way that it does not react itself with the at least one powdery reactive mineral bone cement component. As a basic principle, carrier liquids that are both water-soluble and that have low solubility, as well as those that are water-insoluble, are suitable. Low solubility in water in the sense of the invention is understood to mean carrier liquids whose maximum solubility in water is 1.0 mol/l, preferably 0.1 mol/l. Organic carrier liquids with a maximum solubility in water of more than 1 mol/l (preferably more than 3 mol/l) are designated as water-soluble here. Carrier fluids with low solubility in water are preferred, however. Hydrophobic, practically water-insoluble carrier liquids are especially preferred. The carrier fluid contained in the water-free preparation is preferably bio-compatible.

Additives are preferably used when mixing the reactive mineral bone cement to form a moldable bone cement substance. Surfactants (tensides), active pharmacological substances and fillers, as examples, are additives.

In a preferred design form of the invention, the carrier liquid of the dispersion of the at least one reactive mineral bone cement component for manufacturing a synthetic molded bone replacement element contains surfactants that support or enable the penetration of water or steam or air moisture to initiate and continue the setting reaction; that especially applies when hydrophobic carrier liquids are used. As a preference, the surfactants are selected from the group of tensides and, as a special preference, from the group of nonionic and anionic tensides.

A further component of the moldable bone cement substance is preferably at least one setting accelerator. The setting kinetics are advantageously adjusted and controlled during the hardening of the dispersion as per the invention because of that. Phosphate salts, organic acids or salts of organic acids are preferred setting accelerators. Phosphates containing sodium ions and/or potassium ions or ammonium ions, or salts of organic acids containing sodium ions or potassium ions or ammonium ions, and their mixtures among one another are preferred.

In a particular design form of the invention, the setting accelerator a component of the aqueous solution that initiates the setting process.

In addition, active pharmacological substances can be worked into the moldable bone cement substance. Active pharmaceutical substances with a (bone) growth-stimulating effect or antimicrobial effect are preferred. Active substances selected from antibiotics, antiseptics, antimicrobial peptides, nucleic acids (preferably siRNA), active antiresporbtive substances (preferably bisphosphonates, corticoids, fluorides, proton pump inhibitors), PTH and its derivatives, active bone-growth-stimulating substances, preferably growth factors, vitamins, hormones, morphogenes, with a preference for bone-morphogenetic proteins and peptides, as well as active angiogenetic substances and, especially preferred among them, fibroblast growth factors (aFGF, bFGF, FGF18 etc.), anti-inflammatory substances and anti-tumor substances are especially preferred.

The nucleic acids (especially the siRNA) advantageously exercise a regulatory effect on cells in the proximity of the implanted molded element.

The synthetic molded bone replacement elements as per the invention are especially well suited to being carriers for active pharmacological substances. This is because, on the one hand, the synthetic molded bone replacement element as per the invention is provided at low temperatures (preferably under 80° C., with a special preference for <60° C., and a further preference for <37° C.). This permits active temperature-sensitive substances to be worked in without problems. On the other hand, the method for manufacturing synthetic molded bone replacement elements as per the invention offers improved release of active substances, because the active substances are successively released via the resorption of the mineral bone cement. The method for manufacturing dimensionally stable molded bone replacement elements as per the invention therefore permits a controlled release of active substances in a broad range and is suitable in an especially advantageous way for the use of active, temperature-sensitive substances.

Further preferred components of the moldable bone cement substance, preferably with water-free preparation, are fillers. Water-soluble, particulate fillers made of mineral or organic substances are preferred. The porosity of the solid formed during hardening with water can be advantageously adjusted by the use of water-soluble particles. Water-soluble fillers preferably have a particle size of 10 μm to 2000 μm, and from 100 μm to 1000 μm as a further preference. The water-free preparation preferably contains water-soluble fillers in a proportion of 5 to 90% by volume, with a further preference for 10 to 80% by volume (with reference to the total volume of the water-free preparation/dispersion). Preferred water-soluble fillers are selected from sugars (preferably sucrose), sugar alcohols (preferably sorbitol, xylitol, mannitol), and water-soluble salts (preferably sodium chloride, sodium carbonate, ammonium carbonate or calcium chloride). The proportion of pores of the hardened mineral bone cement is preferably 10 to 90% by volume, with a special preference for 10 to 75% by volume. The pores preferably have a mean pore width (maximum inner extension of a pore) of 100-2000 μm, with a special preference for 100-1000 μm.

As a special preference, all of the components of the dimensionally stable molded bone replacement element can be absorbed into the body. The combination of resorbable metallic or mineral fibers and the reactive mineral bone cement to create the synthetic molded bone replacement elements as per the invention to manufacture composite fiber materials is especially preferred for the invention.

As an option, the moldable bone cement substance contains polymeric additives, preferably selected from chitosan, hyaluronic acid, gelatins, collagen, chondroitin sulfate, cellulose derivatives, starch derivatives, alginate, water-soluble acrylates, polyethylene glycol, polyethylene oxide, PEG-PPG copolymers, polyvinylpyrrolidone, and copolymers made of water-soluble acrylates with polyethylene glycol and/or polyethylene oxide.

As previously mentioned, commercially available cements sometimes contain large amounts of fillers that only superficially participate in the reaction (and thus bind to the cement matrix in particular), but only indirectly participate in the setting process. The participation can, as an example, also consist in a filler acting as a seed crystal for the mineralization during the setting process and therefore influencing the setting kinetics, in particular, but not being converted itself. That applies, for example, in the case of calcium phosphate cements to the addition of precipitated hydroxyl apatite. Cost-effective additives are frequently also added for dilution for economic reasons in technical cements.

As a preference, the setting process is initiated in a saturated steam atmosphere at >90% relative humidity, advantageously controlled by the portion-by-portion supply of a defined amount of water particles, at a temperature between 0 and 100° C., and between 25 and 75° C. as a special preference.

Surprisingly, it was found that the preferred temperature range is significantly below the sintering temperature and an increase in the temperature is associated with neither a quicker setting reactor nor with a quicker increase in compressive strength.

The setting process takes place, as a preference, in a water (steam) atmosphere at >90% relative humidity and a temperature between 0 and 100° C.

The setting process can advantageously take place in multiple steps by first, as an example, having the setting process initiated at a high humidity—>90%—after the shaping step and subsequently carrying out one or more further hardening step(s) under different conditions. In that case, one of the hardening steps can also take place in an aqueous solution. One of the hardening steps (preferably the final one) can also take place under an increased temperature (>100° C.) and under increased pressure (>1 bar) in autoclaves and thus simultaneously serve in the sterilization of the molded elements. Likewise, it is possible to carry out one or more of the setting steps after the interruption of the setting process via withdrawal of water and the washing of the molded elements (and subsequent drying). It is also advantageous in this case to carry out the last setting step via autoclaving, possibly with simultaneous sterilization, advantageously in the final packing It is crucial for the residual hydraulic activity to survive after the execution of all of the setting steps in the final molded bone replacement element as per the invention.

As a preference, the termination of the setting process via a substantial withdrawal of water will take place at a temperature between 0 and 100° C. The substantial withdrawal of water will preferably take place by putting the dimensionally stable molded bone replacement element into contact with an aqueous solvent.

The shaping of the bone cement substance will preferably take place via a (3D) printing process. As a preference, a paste containing reactive mineral bone cement components in a water-free carrier liquid is extruded in the form of sections, put in order and laid down in successive layers (stacked) so that spaces remain between the sections and a 3D molded element with contiguous (interconnecting) porosity arises via the arrangement of the layers, and the dimensionally stable molded bone replacement elements obtained in this way have an overall porosity between 20 and 90%.

The 3D printing process can take place, for instance, in such a way (without being limited by this description in principle) that a previously described dispersion in the form of paste containing a reactive mineral bone cement powder in a water-free carrier liquid is extruded in the form of thin (e.g. 0.3-0.6 mm diameter) sections, put in order and laid down in successive layers (stacked); the successive layers are offset by a pre-specified angle between 0° and 90°, so spaces remain between the sections and a 3D molded element with contiguous (interconnecting) porosity arises via the arrangement of the layers, and the dimensionally stable molded bone replacement elements obtained in this way have an overall porosity between 20 and 90%. Molded elements with almost any desired dimensions and pore arrangements can be printed with this method. Surprisingly, it turned out that a high level of dimensional accuracy of the molded elements is achieved with this method and the subsequent hardening of the printed molded elements in a steam-saturated atmosphere and neither fractures of the sections nor surface changes arose in the individual sections (with most of the other 3D printing methods that are described for ceramic molded elements as bone implants, both shrinkage and other damage in the manufacturing process are described and, in particular, significantly narrower limitations with small land thicknesses and small pore dimensions).

As a preference, the complete hardening of the synthetic molded bone replacement element with residual hydraulic activity or of a preform will take place—after the first partial hardening and water withdrawal—via renewed contact with an aqueous liquid containing biological components and/or active pharmacological substances and/or isolated or cultivated cells.

The bone cement mass will preferably be shaped via a granulation process in which the dimensionally stable molded bone replacement element is obtained in the form of granules consisting of individual granules or agglomerations of granules. The granules are produced in a known way, for instance via fluidized bed granulation or granulation via an extrusion process. During the granulation via an exclusion process, the pasty dispersion comprised of a reactive mineral cement powder and a water-free carrier liquid is pressed out of a cartouche through a calibrated outlet opening. The extruded section is sheared off at short intervals, and cylindrical segments of the paste are obtained in this way that can subsequently be rounded off on a dish granulator. The granules obtained in this way can be hardened and compacted.

The invention also relates to the use of a dimensionally stable molded bone replacement element for manufacturing an alloplastic implant.

Use of a dimensionally stable molded element as a carrier material in the cell culture, the tissue culture and/or the tissue engineering.

Molded elements with residual hydraulic activity as per the invention can be used in a variety of ways, especially as a cell-culture carrier for the cultivation of bone cells in research or for tissue engineering. Further preferred applications are as carrier materials in biotechnology; the cultivated bacteria or yeast cells can, for instance, already be put into the carrier material in the manufacturing process. A further preferred application is the purification of (waste) water from heavy metals and organic substances.

Use as an alloplastic implant material for filling in bone defects that can be congenital, that can arise as a result of accidents or that can arise after surgical procedures—especially after the removal of bone tumors or cysts, change of a prosthesis, corrective osteotomies etc.—is a special preference. The use of the molded bone replacement elements as per the invention in mouth/jaw surgery to build new bone, e.g. alveolar ridge augmentation, a sinus lift or filling in extraction holes, is a special preference.

Another special preference is the use of the molded bone replacement elements as per the invention in orthopedics, trauma surgery and spinal column surgery to fill in all types of bone defects. In comparison with other biological and alloplastic bone replacement materials currently in use, the molded bone replacement elements as per the invention offer the advantage of defined porosity, increased bioactivity, defined mechanical characteristics, simple intra-operative processing capability and ease of combination with biological substances, bone cells and active pharmacological substances.

Use of the molded bone replacement elements as per the invention within the framework of therapeutic tissue engineering is a special preference. Molded bone replacement elements as per the invention are incubated in vitro with bone cells (preferably autologous bone cells or stem cells) under sterile conditions for this; the dimensionally stable molded bone replacement elements are populated with the cells, and the cells can be reproduced. After the conclusion of the cultivation, an autologized bone replacement implant is obtained that is indicated for the regeneration of major bone defects, in particular.

The combination of molded elements with bone cells or stem cells preferably takes place in a bioreactor; the molded elements as per the invention bring along especially good prerequisites for this, in particular—aside from the above-mentioned characteristics—variable shaping without a technological size limitation with, at the same time, completely interconnected porosity that is a crucial requirement for good perfusion with a culture medium in the bioreactor.

BRIEF DESCRIPTION OF THE DRAWINGS

The invention is to be explained in more detail with the aid of the descriptions and examples that are provided without limiting it to them; the figures show the following.

DETAILED DESCRIPTION OF THE PREFERRED EMBODIMENTS

Example 1

Figure 1A:
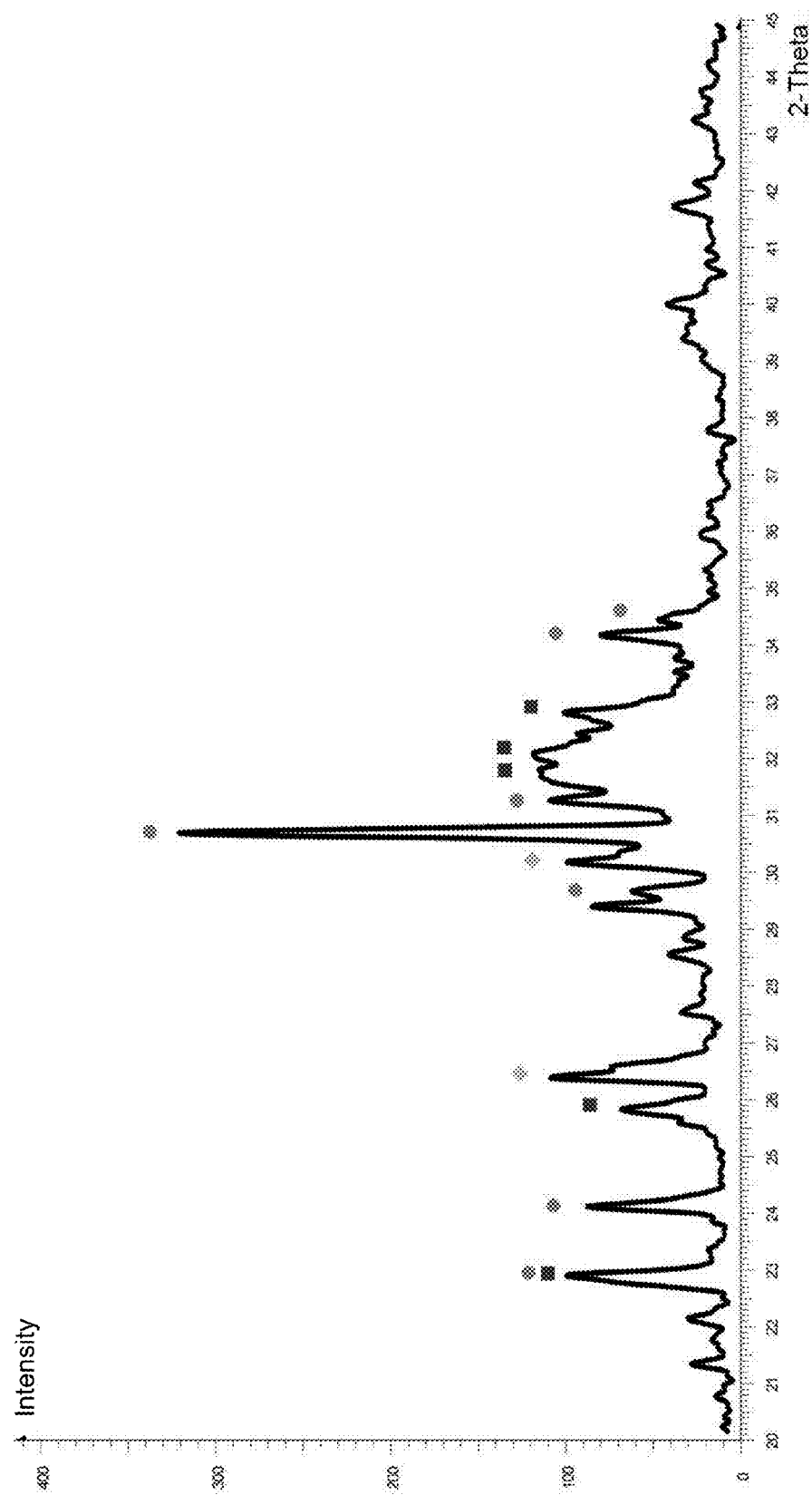
FIG. 1A) X-ray diffractogram of a porous, printed molded element made of paste CPC that was hardened for 2 days under steam saturation at 50° C. and whose hardening was subsequently stopped via removal of water with acetone (3×20 min. acetone washing in the ratio 1:5 w/w) and drying at 80° C. The reflexes show, as the predominant crystalline phase, α-TCP (●) and a broad reflex for nanocrystalline hydroxyl apatite (■) that arises as a reaction product of the hydraulic setting reaction. A further reactive component is the monetite (♦). whose reflexes can still be clearly recognized. The reaction was stopped before the complete hydraulic setting.

1.1 Mixing a Reactive Mineral Bone Cement to Create a Moldable Bone Cement Substance A calcium phosphate cement powder based on α-TCP was manufactured by mixing 60 g of α-tricalcium phosphate, 26 g of calcium hydrogen phosphate (water free), 10 g of calcium carbonate and 4 g of hydroxyl apatite and then finely grinding it. 2.5 g of ground dibasic potassium phosphate was added to 82 g of this powder mixture, and this was then dispersed in 15.5 g of an oil-emulsifying agent mixture comprised of short-chain triglycerides (Milyol 812), caster oil ethoxylate (Cremophor ELP) and cetyl phosphate (Amphisol A) (ratio of ingredients w/w 82:13:5). The mixture that was obtained was mixed to form a plastically deformable paste and ground up. After the conclusion of the grinding process, the paste was filled into commercially available 5 ml PE cartouches and stored until further use.

1.2 Shaping

The 5 ml PE cartouches filled with the paste that was described were connected via their Luer Lock connector to a stainless steel cannula with an internal diameter of 0.3 mm and mounted in a commercially available 3D printer (regenHU, Switzerland). A section of the plastically deformable paste was pressed through the cannula with compressed air and set down in layers on a glass plate according to a computer-controlled system. The porosity of the printed molded elements was specified by the choice of the section spacing. The successive layers were offset by an angle of 90°. The consistency of the paste that was described made it possible to print molded elements with a height of 15 mm without a recognizable deformation of the lower sections. Molded elements with the dimensions 10×10×5 mm were manufactured in the chosen example. The overall porosity was approx. 60%.

1.3 Hardening of the Molded Elements

After the conclusion of the printing process, the glass plate with the printed molded element was put into a Petri dish. The Petri dish was put into a waterproof foil bag that additionally contained a water-saturated sponge. The foil bag was tightly closed. The water-saturated sponge and the printed molded element did not have direct contact. The molded elements that were packed in this way were incubated in an incubator at 50° C. for various periods of time.

1.4 Termination of the Setting Reaction

To terminate the setting reaction, the molded elements were removed from the incubator at different points in time and put into a glass vessel with water-free acetone for 20 in. (ratio of acetone to the molded element: 5:1 (w/w)) and lightly shaken. The process was repeated 3× to remove both water and the oil-emulsifying agent mixture. After the last washing in acetone, the molded elements were dried at 80° C. in the drying cabinet and then packed in foil bags in an airtight manner.

1.5 Analysis of the Dimensionally Stable Molded Elements with Regard to their Compressive Strength and Material Conversion in Dependence Upon the Duration of the Setting Reaction The table below shows the compressive strength of the molded elements that were manufactured in dependence upon the hardening duration at 50° C. and saturated air moisture. The compressive strength was determined for molded elements with the dimensions 10×10×5 mm (horizontal). The molded elements of the example had a density of approx. 1.1 g/cm³ on average. The measurement took place in a universal testing machine of the company Hegewald & Peschke using a 20 kN load cell at a feed rate of 1 mm/min. The material conversion in dependence upon the hardening duration at 50° C. and saturated air moisture was investigated via XRD measurements (x-ray diffractograms).

TABLE 1

Compressive strength values (CS-MV) of 7 test specimens each that were hardened at 50° C. and saturated air moisture.

| Time | CS-MV [MPa] |
|---|---|
| 6 h | 1.72 |
| 16 h | 5.25 |
| 24 h | 5.85 |
| 38 h | 6.40 |
| 48 h | 11.44 |
| 4 d | 10.38 |
| 7 d | 10.64 |
| 14 d | 11.50 |

The joint analysis of the progression of compressive strength and the material conversion of the mineral phases in the course of the setting reaction shows that the increase in mechanical strength takes place in a substantially quicker way than would be expected after the material conversion of the mineral starting components into hydroxyl apatite, the reaction product of the setting reaction. In particular, the compressive strength values already show the maximum value of the compressive strength after 48 h, whereas the material conversion of the reactive starting components has not come anywhere close to being concluded and is at <50% based on the X-ray diffractogram.

Figure 1B:
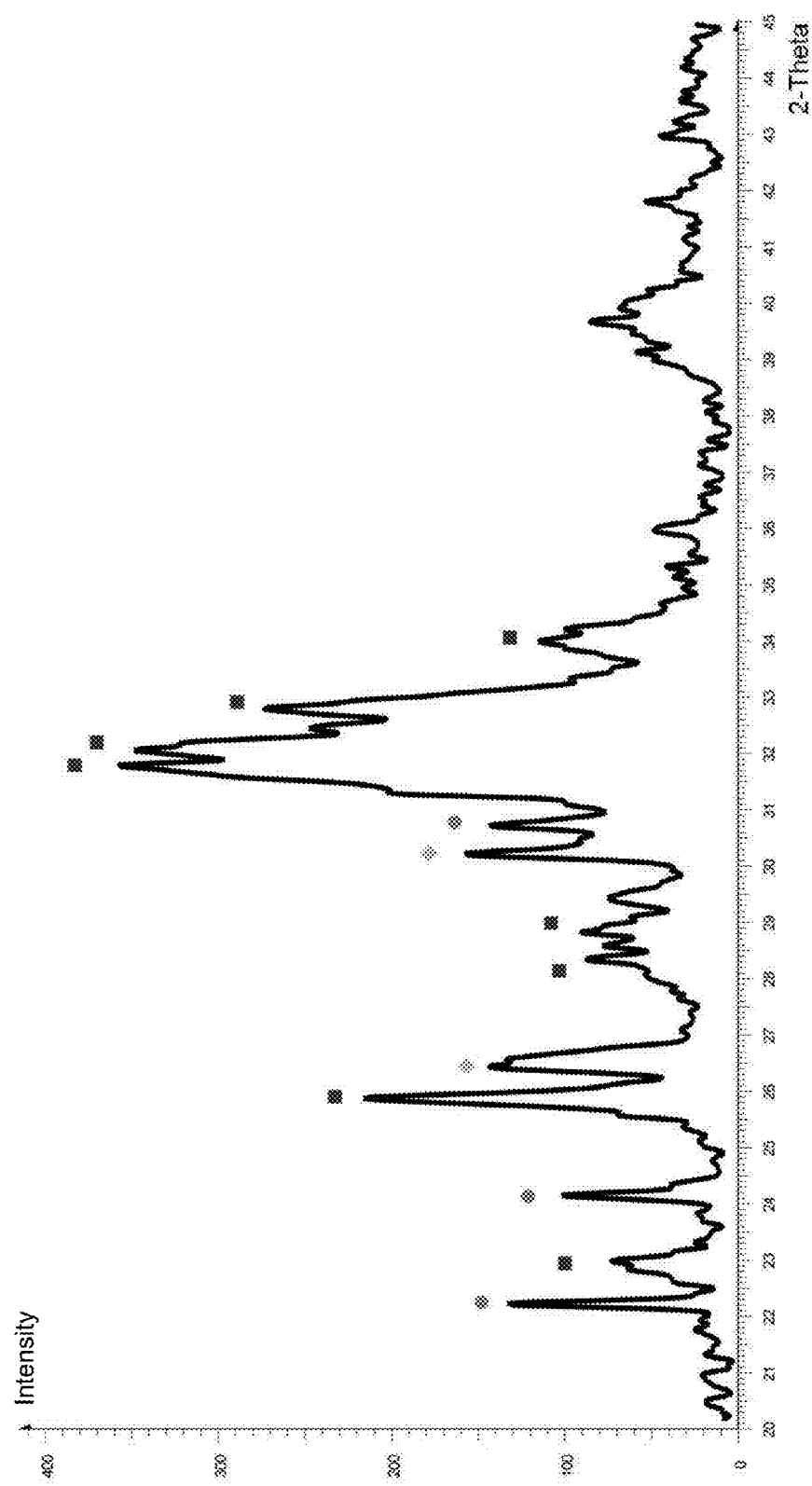
FIG. 1B) X-ray diffractogram of a porous, printed molded element made of paste CPC that was hardened for 14 days under steam saturation at 50° C. and whose hardening was subsequently stopped via removal of water with acetone (3×20 min. acetone washing in the ratio 1:5 w/w) and drying at 80° C. The reflexes show the presence of only slight amounts of α-TCP (●) and monetite (♦) as a sign of almost completely concluded hydraulic conversion. The dominant phase is nanocrystalline hydroxyl apatite (■), which is characterized by the broad reflex between 31.5 and 33.5°.

The degree of conversion in this comparison is determined with the aid of the content of α-TCP determined via X-ray diffractometry or more specifically the ratio of α-TCP to hydroxyl apatite at the respective points in time of the measurements (FIGS. 1A and 1B). The starting content of all of the reactive mineral components was 96%; the starting content of α-TCP in the reactive mineral powder mixture was 60%. After 48 h, the content of α-TCP was determined to be approx. 45%, whereas the remaining overall content of all of the reactive mineral powder components was approx. 50%. After 14 days, the material conversion to hydroxyl apatite was almost completely concluded under the selected conditions; only traces of α-TCP were able to be verified via X-ray diffractometry (FIG. 1b). A further increase in strength is not associated with the continuing conversion, though.

The analysis of the progression of compressive strength makes a targeted selection of product characteristics possible with respect to the intended application. The hardening was stopped via water withdrawal at an early point in time for the simplest possible processing capabilities that were desired and the greatest conversion under biological conditions that was strived for. In the case of the molded elements of the example, that could already take place after approx. 6 h, because sufficient dimensional stability of the printed molded element has already been achieved at this point in time; a strength of approx. 2 MPa is strived for. A termination of the setting reaction after approx. 16 h is preferred, when the strength is approx. 50% of the maximum strength. A termination of the setting reaction in the case of the molded elements of the example after approx. 48 h, when the strength has reached 100% or nearly 100% of the maximum strength, is especially preferred. In so doing, the point in time of the termination of the setting reaction is chosen in such a way that a value for the material conversion that is as small as possible exists at this point in time. Experimental data have shown that this circumstance is reached for the molded element in the example at approx. 48 h. An optimal compromise can be achieved between strength and biological activity in that way.

Figure 2:
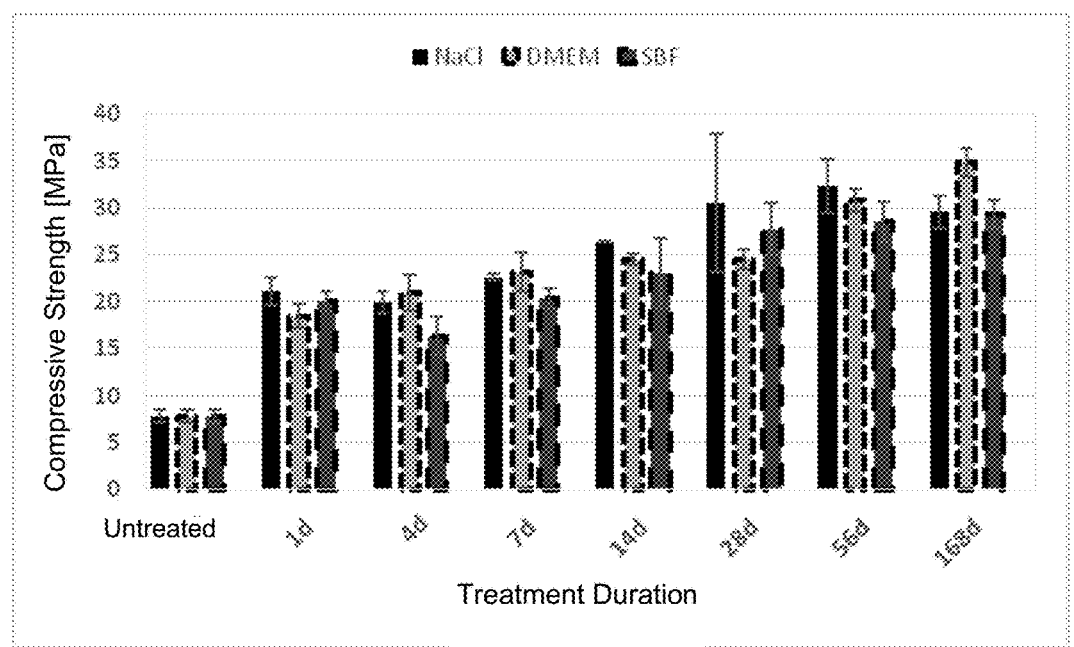
FIG. 2) Strength progression after different incubation times in different aqueous media of the dimensionally stable molded bone replacement elements manufactured according to Example 1.6.

1.6. Conversion of the Molded Elements with Residual Hydraulic Activity After Incubation in Different Media Molded elements with the dimensions 10×10×5 mm with the material composition according to Example 1.1 were manufactured in a 3D printing process according to Example 1.2 and hardened over 24 h according to Example 1.3 and the hardening was terminated via water withdrawal according to Example 1.4 in such a way that the average density was 1.5 g/cm³. After that, the molded elements were packed in an air-tight way in foil bags and stored for further investigation at room temperature. The molded elements manufactured in that way had a compressive strength of 7.8 MPa. Three of the molded elements each (per medium and investigation point in time) were put into different media (NaCl, DMEM (cell culture medium) and SBF (simulated body fluid) to investigate the influence of the media composition on the further hardening of the molded elements; the incubation took place at 37° C. FIG. 2 shows the strength progression after different incubation times. The strength of the molded elements already increases strongly in all of the media after a short period of incubation. The increase continues over the entire investigation period of 168 days and reaches unexpectedly high values at approx. 30-35 MPa. There are no significant differences with regard to the progression of strength between the different incubation media that differ significantly in terms of composition. The results show that the setting reaction interrupted via water withdrawal is continued after being put into an aqueous medium once again and that the further reaction is independent of the composition of the medium to a great extent (in so far as the composition of the medium is within the biologically relevant framework).

Example 2—Study Involving Implantation in a Sheep

Printed molded elements according to Example 1 after 4 days of hardening were shaped via milling into half spheres with a radius of 5 mm, subsequently washed in water and acetone, dried, and, after that, individually packed in plastic tubes and sterilized with 25 kGy via gamma irradiation. In the technique according to Busenlechner (Biomaterials 29 (2008) 3195-3200), the half spheres from the printed molded elements were put in a positive-locking way into titanium half spheres with an inner width of 10 mm and, after placing 11 small drill holes each of 1 mm diameter and 2 mm depth, set on the calvarias of full-grown sheep. The control group received half spheres that were filled with porous β-TCP (bone replacement material according to the prior art). After 8 and 16 weeks, the implants were removed and evaluated on a histological basis. The group with the printed molded elements showed a significantly stronger formation of new bone than the group with β-TCP. Although practically all of the pores of the printed molded elements were filled with new bone and all of the surfaces of the material as per the invention were covered with new bone, this was only sporadically the case with the β-TCP. These in vivo results show the exceptionally high bioactivity of the material as per the invention in comparison with a molded bone replacement element used on a standard basis in orthopedics and traumatology. The results of the study confirm that the formation of nanocrystalline hydroxyl apatite leads under biological conditions to a material with an especially high level of bioactivity. This high level of bioactivity is reflected in a significantly increased rate of new bone formation in a clinically relevant model for bone healing. A β-TCP that is comparable to the implant material as per the invention with regard to the molar calcium/phosphate ratio (approx. 1.5) and the overall porosity served as a comparative implant. The significantly increased formation of new bone and bone integration that was likewise significantly quicker and more complete can therefore be causally traced back to the greater bioactivity by the composition as per the invention and the method of manufacturing the molded element with residual hydraulic activity that was described.

Example 3—Molded Element with Residual Hydraulic Activity on the Basis of Magnesium Calcium Phosphate Cement (MgPCP)

Figure 3:
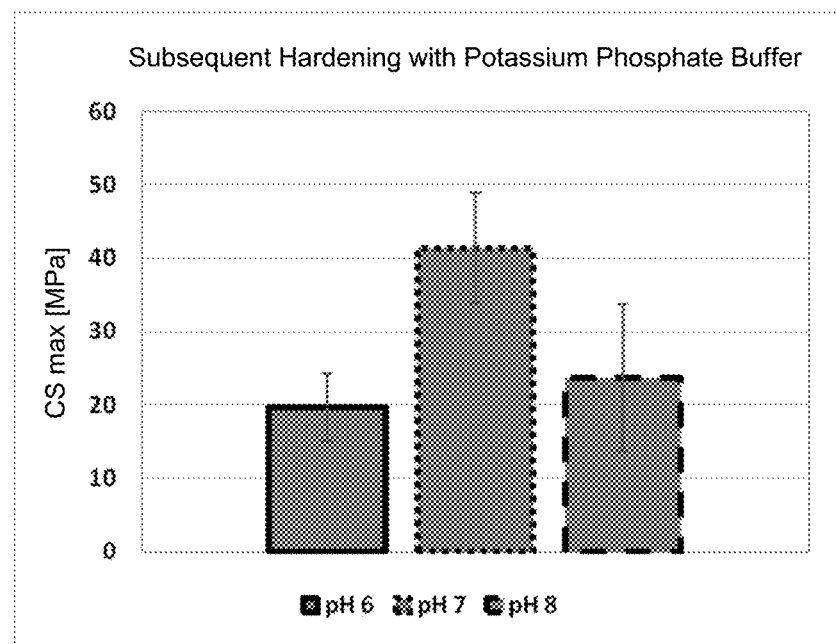
FIG. 3) Compressive strength (CS) of the molded elements in dependence upon the pH value of the incubation solution.

In a manner analogous to Example 1, cement pastes based on MgCPC were produced by creating, with the same organic phase, the mineral phase from MgCPC powder with the composition $(Ca_{0.5}Mg_{2.5}(PO_4)_2)$ in a ratio of 84% by weight powder to 16% by weight carrier liquid. The shaping likewise took place in a manner analogous to Example 1 via a 3D printer to create molded elements with the dimensions 10×10×5 mm with a mean density of 1.4 g/ml. The initial hardening of the molded elements took place in a saturated steam atmosphere at 37° C. over 24 h. After that, the molded elements were incubated in various media to investigate the influence of the medium composition. The compressive strength of the molded elements is presented in FIG. 3 in dependence upon the pH value of the incubation solution. The result shows that MgCPC molded elements with residual hydraulic activity can be manufactured with a relatively high level of initial strength that can subsequently (after termination of the hardening via water withdrawal) be further strengthened by incubation over 24 h in a defined buffer solution (the reference had a compressive strength of 17 MPa).

Example 4—Setting of Molded Elements Over Several Stages

CPC molded elements with the dimensions 6×6×12 mm are prepared by plastering paste in CPC into a divisible metal mold and holding it over 24 h at 37° C. in a 0.9% NaCl solution. After removal from the mold, the molded elements are washed in distilled water and dried. The compressive strength is approx. 12 MPa. Cylinders dimensioned with the diameter 5 mm and the height 12 mm are manufactured from these low-grade hardened molded elements on a lathe. After that, the cylinders are incubated for 2 days at 37° C. in 1% CaCl2 solution, washed with acetone and dried. The compressive strength is 32 MPa. The molded elements that are obtained in this way are subsequently put into simulated body fluid at 37° C. for 7 days, water is subsequently withdrawn from them in acetone and they are dried. The compressive strength is 56 MPa. The degree of conversion according to the XRD analysis is approx. 85%.

The molded elements can—depending on the intended use—be used as a product after each of the steps that were described.

The invention claimed is:

1. Method for manufacturing dimensionally stable molded bone replacement elements with residual hydraulic activity, comprising the following steps:
   a. mixing a reactive mineral bone cement with a carrier fluid with low solubility in water to create a moldable bone cement substance,
   b. shaping the bone cement substance to form a molded bone replacement element,
   c. putting the molded bone replacement element into contact with an aqueous solution or a water (steam) saturated environment so that a setting process is initiated and the molded bone replacement element achieves at least 5% of the maximum value of the strength of a completely hardened bone replacement material made of the same components and with the same structural features, especially the same porosity,
   d. termination of the setting process by a complete withdrawal of physically bound and condensed water so that the dimensionally stable molded bone replacement element, which can be converted under biological conditions, 37° C. and water saturation, contains a share of hardened mineral bone cement of 5% to 90% by weight, such that the dimensionally stable molded bone replacement element has residual hydraulic activity.

2. Method according to claim 1, characterized in that the molded bone replacement element is dried via the removal of auxiliary materials, residual water and/or water-soluble solvents contained in it that were used to withdraw water.

3. Method according to claim 1, characterized in that a substance from the group of silicates, phosphates, sulfates, carbonates, oxides and/or hydroxides in combination with calcium ions, magnesium ions and/or strontium ions, which can set in a hydraulic setting process to form a solid of low solubility when put into contact with an aqueous solution or after addition to an aqueous solution, is used as at least one reactive mineral bone cement component for mixing the reactive mineral bone cement.

4. Method according to claim 1, characterized in that additives are used when mixing the reactive mineral bone cement to create a moldable bone cement substance.

5. Method according to claim 1, characterized in that the aqueous solution contains at least one additive selected from a buffer solution, an organic and/or an inorganic salt, a cell preparation, an active biological, recombinant or pharmacological substance, nucleic acid (RNA or DNA), mixtures of nucleic acids, an amino acid, a modified amino acid, a vitamin and mixtures of them.

6. Method according to claim 1, characterized in that the setting process is initiated in an atmosphere at >90% relative humidity and a temperature between 0° C. and 100° C.

7. Method according to claim 1, characterized in that the termination of the setting process via the substantial withdrawal of water takes place at a temperature between 0° C. and 100° C.

8. Method according to claim 1, characterized in that the setting reaction of the molded elements is carried out in several steps and/or with different aqueous solutions and/or a steam atmosphere.

9. Method according to claim 1, characterized in that the bone cement substance is shaped via a (3D) printing method.

10. Method according to claim 1, characterized in that the bone cement substance is shaped via a granulation process.

11. Method according to claim 1, comprising the further step of applying the dimensionally stable molded bone replacement elements as alloplastic implants in a human body.

12. Method according to claim 1, comprising the further step of applying the dimensionally stable molded bone replacement elements as carrier materials in the areas of cell culture, tissue culture and/or tissue engineering.

13. Method according to claim 1, wherein the water is withdrawn via a variation of physical environmental parameters.

14. Method according to claim 1, wherein the water is withdrawn via contact of synthetic bone replacement material with a water-soluble solvent.

15. Method according to claim 1, wherein the water is withdrawn via consumption in a chemical setting reaction such that a complete conversion of physically bound water into chemically bound water is brought about.

* * * * *